United States Patent
Bonnet et al.

(10) Patent No.: US 6,447,509 B1
(45) Date of Patent: Sep. 10, 2002

(54) TRANSURETHRAL DISSECTION ELECTRODE

(75) Inventors: Ludwig Bonnet, Knittlingen; Rolf Muschter, Worth, both of (DE)

(73) Assignee: Richard Wolf GmbH, Knittlingen (DE)

( * ) Notice: Subject to any disclaimer, the term of this patent is extended or adjusted under 35 U.S.C. 154(b) by 120 days.

(21) Appl. No.: 09/614,858

(22) Filed: Jul. 12, 2000

(30) Foreign Application Priority Data

Aug. 5, 1999 (DE) .......................... 299 13 688

(51) Int. Cl.[7] .............................. A61B 18/18
(52) U.S. Cl. .................... 606/45; 606/47; 606/41; 606/28
(58) Field of Search .............. 606/45, 47, 41, 606/29, 28, 27, 48; 607/101, 99, 98, 96; D24/144, 170, 187; 600/372, 373, 374

(56) References Cited

U.S. PATENT DOCUMENTS

| | | | |
|---|---|---|---|
| 5,330,470 A | * | 7/1994 | Hagen .................. 606/42 |
| 5,344,420 A | * | 9/1994 | Hilal et al. .............. 606/16 |
| 6,306,134 B1 | * | 10/2001 | Goble et al. ............ 606/34 |

* cited by examiner

*Primary Examiner*—Linda C. M. Dvorak
*Assistant Examiner*—Kenneth G Schopfer
(74) *Attorney, Agent, or Firm*—Akin, Gump, Strauss, Hauer & Feld, L.L.P.

(57) ABSTRACT

The transurethral dissection electrode has a shank and an electrode head located at the distal shank end. The electrode head essentially consists of at least one distally tapering truncated cone body with two oppositely lying flattenings.

7 Claims, 1 Drawing Sheet

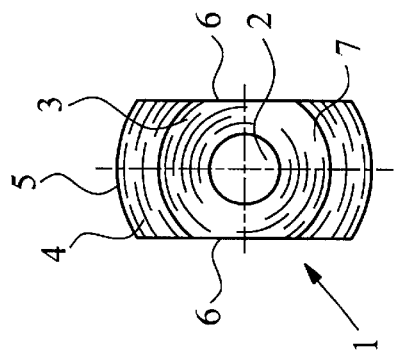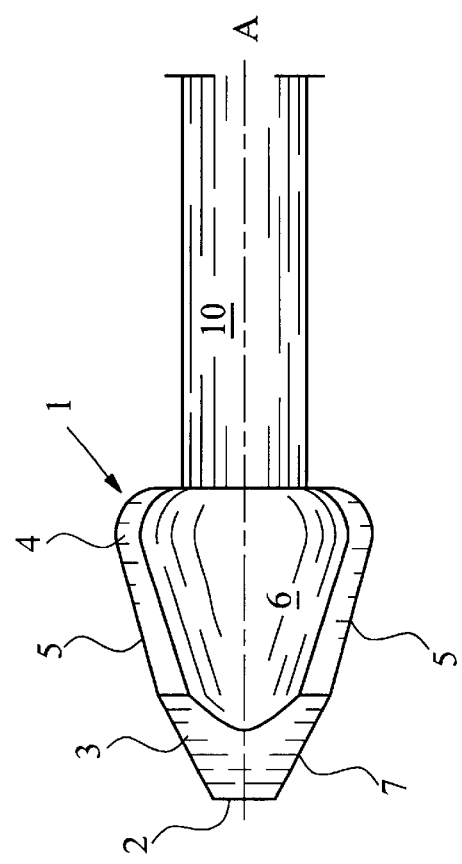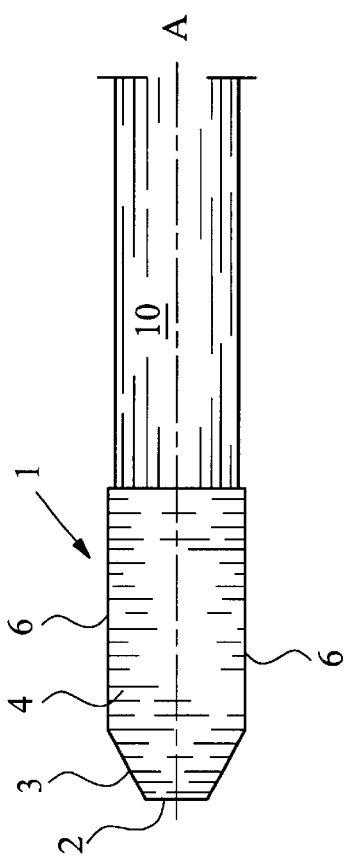

TRANSURETHRAL DISSECTION ELECTRODE

BACKGROUND OF THE INVENTION

The invention relates to a transurethral dissection electrode with a shank and with an electrode head located at the distal shank end.

With adenomas of the prostrate occurring relatively often, particularly with elder men, because the free lumen of the urethra is continuously reduced by the growth of the adenoma, it is necessary for this ademona to be removed in order to prevent a complete closure of the urethra. The adenoma is not formed annular but is composed of several individual growths of differing sizes.

The removal of these individual growths until the present day has been effected in that by way of resectoscope loops the adenoma tissue is removed in a strip-like manner under endoscopic control. This type of removal of the adenoma tissue is relatively time-consuming and disadvantageous since for example a blood vessel in the adenoma tissue on removal is severed several times. By way of this continuous new quantities of blood get into the rinsing fluid located in the bladder and limit the view of the operator by way of the endoscope optic to a great extent. Since the contaminated rinsing fluid must be continuously led away and fresh rinsing fluid must be supplied, the duration of the endoscopic operation is lengthened which leads to unnecessary burdening of the patient and the operating personnel.

For a few years one has attempted to replace this so-called HF-resection of the prostate by laser, wherein the adenoma tissue proceeding from the sphincter, close to the ademona capsule, is practically peeled out in the direction of the neck of the bladder. This manner of proceeding is very tedious and also has the significant disadvantage that for this as a rule a relatively expensive laser must be provided, for which also there arise corresponding maintenance costs.

BRIEF SUMMARY OF THE INVENTION

Proceeding from the known state of the art it is the object of the invention to provide a generic transurethral dissection electrode with which the prostrate adenoma without laser resection may be simply and effectively released from the inner wall of the urethra, close to the adenoma capsule, in order to be able to reduce the endoscopic operation burdening the patient to a great extent.

According to an essential aspect of the invention the dissection electrode according to the invention is wherein the electrode head essentially consists of at least one truncated cone body tapering distally with two oppositely lying flattenings.

With one embodiment example the electrode head distally ends in a circular surface. The head proximally in relation to the electrode longitudinal axis has larger radial dimensions than the cylindrical shank and here is designed atraumatically by way of rounding. By way of the design of the transurethral dissection electrode with the two flattenings lying opposite one another the safety on removal with a simultaneously good vaporization of the tissue as with a laser resection is increased. Furthermore this dissection electrode permits a good view of the field of operation.

With the transurethral dissection electrode according to the invention the adenoma is now no longer removed in layers but released from the so-called prostrate capsule. After an effected separation from the urethra inner wall the individual adenoma growths as a whole or after an effected severing may be easily removed from the urethra in the longitudinal direction.

The detachment of the adenoma is effected in that the electrode head is introduced between the urethra walling and the relatively rigid tissue surrounding the adenoma, thus the prostrate capsule. With this the tissue vaporizes in the region of the electrode head which is pivoted to and fro laterally along the capsule as well as is led in the direction of the bladder. By way of vaporization of the tissue in the region of the electrode the thus created gap is at least partly visible. By way of the low space requirement of the electrode, relatively little tissue is to be vaporized so that the electrode need only be operated with low electric energy.

With one embodiment example the electrode head essentially consists of two truncated cone bodies which form a unit, lie on the electrode longitudinal axis and in each case taper distally, and the flattenings extend proceeding from the first truncated cone body bodering the shank up to the second truncated cone body, wherein the first truncated cone body has a smaller acute angle than the second truncated cone body.

In an alternative embodiment form the flattenings may be formed in a manner such that they run distally inclined to one another with the same angle to the electrode longitudinal axis.

BRIEF DESCRIPTION OF THE DRAWINGS

The invention is hereinafter described by way of an embodiment example shown in the drawing. There is shown:

FIG. 1 a level plan view of a dissection electrode provided with an electrode head formed according to the invention, FIG. 2 a plan view of the distal end of the electrode head of the dissection electrode shown in FIG. 1 and FIG. 3 a lateral view of the dissection electrode represented in FIGS. 1 and 2.

DETAILED DESCRIPTION OF THE INVENTION

With the dissection electrode represented in the FIGS. 1 to 3 in various views the electrode head 1 connecting axially to the shank 10 consists of two distally tapering truncated cone bodies 4, 3 bordering one another, of which the first truncated cone body 4 connecting to the shank 10 has a smaller acute angle than the second truncated cone body 3. The electrode head 1 proximally, where it connects to the shank, is rounded atraumatically and has at this location with respect to the electrode longitudinal axis A larger radial dimensions than the cylindrical shank 10.

According to FIG. 2 the electrode head 1 on the distal side ends in a circular surface 2, and the two flattenings 6 lying opposite one another are plane and lie symmetrically and parallel to the electrode longitudinal axis A.

The conical outer sides 5 and 7 of the truncated cone bodies 4, 3, likewise lie symmetrically to the electrode longitudinal axis A. As the FIGS. 1 and 2 show, the flattenings 6 from the first truncated cone body 4 blend into the second truncated cone body 3. The lateral view in FIG. 3 clearly shows that the mutual distance of the flattenings 6 corresponds roughly to the diameter of the shank 10.

It is yet to be mentioned that the two planes of symmetry, specifically the plane of symmetry of the flattenings 6 and of the conical outer sides 5, 7 of the electrode head 1 stand perpendicularly on one another.

With the manufacture of the dissection electrode one proceeds from a rotation body of metal comprising two truncated cone bodies 4, 3 connected to one another, on which one then creates the flattenings 6 for example by milling or grinding.

Although in the above described embodiment example of a transurethral dissection electrode the electrode head 1 is formed of two truncated cone bodies 4, 3 and two plane flattenings symmetrical to one another and lying parallel to the electrode longitudinal axis A, this is not a compellingly necessary feature. Instead of this the electrode head 1 may consist of a single truncated cone body. Likewise the flattenings 6 may distally run inclined to one another at the same angle to the electrode longitudinal axis.

We claim:

1. A transurethral dissection electrode comprising a shank and an electrode head located at a distal end of the shank, wherein the electrode head comprises at least one distally tapering truncated cone body with two oppositely lying flattenings.

2. A transurethral dissection electrode comprising a cylindrical shank and an electrode head located at a distal end of the shank, the electrode head comprising at least one distally tapering truncated cone body with two oppositely lying flattenings, wherein the electrode head ends distally in a circular surface, wherein at a proximal end the electrode head has a larger radial dimension than the cylindrical shank, and wherein the proximal end of the electrode head is rounded atraumatically.

3. The dissection electrode according to claim 2, wherein the flattenings run parallel to one another.

4. The dissection electrode according to claim 2, wherein the flattenings run distally inclined to one another at a same angle with respect to a longitudinal axis of the electrode.

5. A transurethral dissection electrode comprising a cylindrical shank and an electrode head located at a distal end of the shank, the electrode head comprising first and second distally tapering truncated cone bodies which form a unit, each cone body having two oppositely lying flattenings, wherein the truncated cone bodies lie on a longitudinal axis of the electrode, wherein the flattenings, proceeding from the first truncated cone body bordering the shank, extend up to the second truncated cone body, and wherein the tapering of the first truncated cone body has a smaller acute angle relative to the longitudinal axis than the tapering of the second truncated cone body.

6. The dissection electrode according to claim 5, wherein the flattenings run parallel to one another.

7. The dissection electrode according to claim 5, wherein the flattenings run distally inclined to one another at a same angle with respect to the longitudinal axis of the electrode.

* * * * *